US010525260B2

(12) United States Patent
Masson et al.

(10) Patent No.: US 10,525,260 B2
(45) Date of Patent: Jan. 7, 2020

(54) ELECTRODES AND ELECTRODE POSITIONING SYSTEMS FOR TRANSVASCULAR NEUROMODULATION

(71) Applicant: NeuroTronik IP Holding (Jersey) Limited, St. Helier (JE)

(72) Inventors: Stephen C Masson, Raleigh, NC (US);
Scott Purcell, Durham, NC (US);
Michael Cuchiara, Durham, NC (US);
Richard A. Glenn, Santa Rosa, CA (US)

(73) Assignee: NeuroTronik IP Holding (Jersey) Limited, St. Helier (JE)

( * ) Notice: Subject to any disclaimer, the term of this patent is extended or adjusted under 35 U.S.C. 154(b) by 0 days.

(21) Appl. No.: 14/820,536

(22) Filed: Aug. 6, 2015

(65) Prior Publication Data
US 2018/0126151 A1 May 10, 2018

Related U.S. Application Data

(60) Provisional application No. 62/034,144, filed on Aug. 6, 2014, provisional application No. 62/034,146, filed on Aug. 6, 2014, provisional application No. 62/034,142, filed on Aug. 6, 2014, provisional application No. 62/036,526, filed on Aug. 12, 2014, provisional application No. 62/034,149, filed on Aug. 7, 2014, provisional application No. 62/034,152, filed on Aug. 7, 2014.

(51) Int. Cl.
*A61N 1/05* (2006.01)

(52) U.S. Cl.
CPC .................................. *A61N 1/056* (2013.01)

(58) Field of Classification Search
None
See application file for complete search history.

(56) References Cited

U.S. PATENT DOCUMENTS

| | | | |
|---|---|---|---|
| 5,722,401 A | 3/1998 | Pietroski et al. | |
| 5,911,739 A | 6/1999 | Kordis et al. | |
| 6,216,043 B1* | 4/2001 | Swanson | A61B 5/0422 600/374 |
| 8,644,902 B2* | 2/2014 | Kordis | A61B 5/0422 600/374 |
| 2006/0111702 A1 | 5/2006 | Oral et al. | |
| 2006/0229687 A1 | 10/2006 | Goetz et al. | |
| 2008/0004675 A1 | 1/2008 | King et al. | |
| 2010/0036451 A1 | 2/2010 | Hoffer et al. | |
| 2012/0239109 A1 | 9/2012 | Lee | |

(Continued)

OTHER PUBLICATIONS

International Search Report for PCT/US15/44112 (WO2016/022867), dated Jan. 28, 2016.

(Continued)

*Primary Examiner* — Brian T Gedeon

(57) ABSTRACT

Electrode systems for transvascular stimulation of target nerves include electrode arrays, elements promoting blood flow between electrode surfaces and surrounding vascular walls, electrodes shaped to promote more even current density than electrodes having angular edges, features for retaining the electrode systems with blood vessels, and features for using electrode-carrying elements to asymmetrically distend blood vessel walls towards target nerve structures.

3 Claims, 16 Drawing Sheets

(56) References Cited

U.S. PATENT DOCUMENTS

| | | |
|---|---|---|
| 2013/0006282 A1 | 1/2013 | Wilkinson et al. |
| 2013/0282084 A1 | 10/2013 | Mathur et al. |
| 2014/0142590 A1 | 5/2014 | Masson et al. |
| 2014/0200579 A1 | 7/2014 | Cooke et al. |

OTHER PUBLICATIONS

European Search Report for EP 15829460.3 (European National Phase of PCT/US15/44112), dated Apr. 4, 2018.
Australian Examination Report for AU2015300886 (Australian National Phase of PCT/US15/44112), dated Mar. 12, 2019.

* cited by examiner

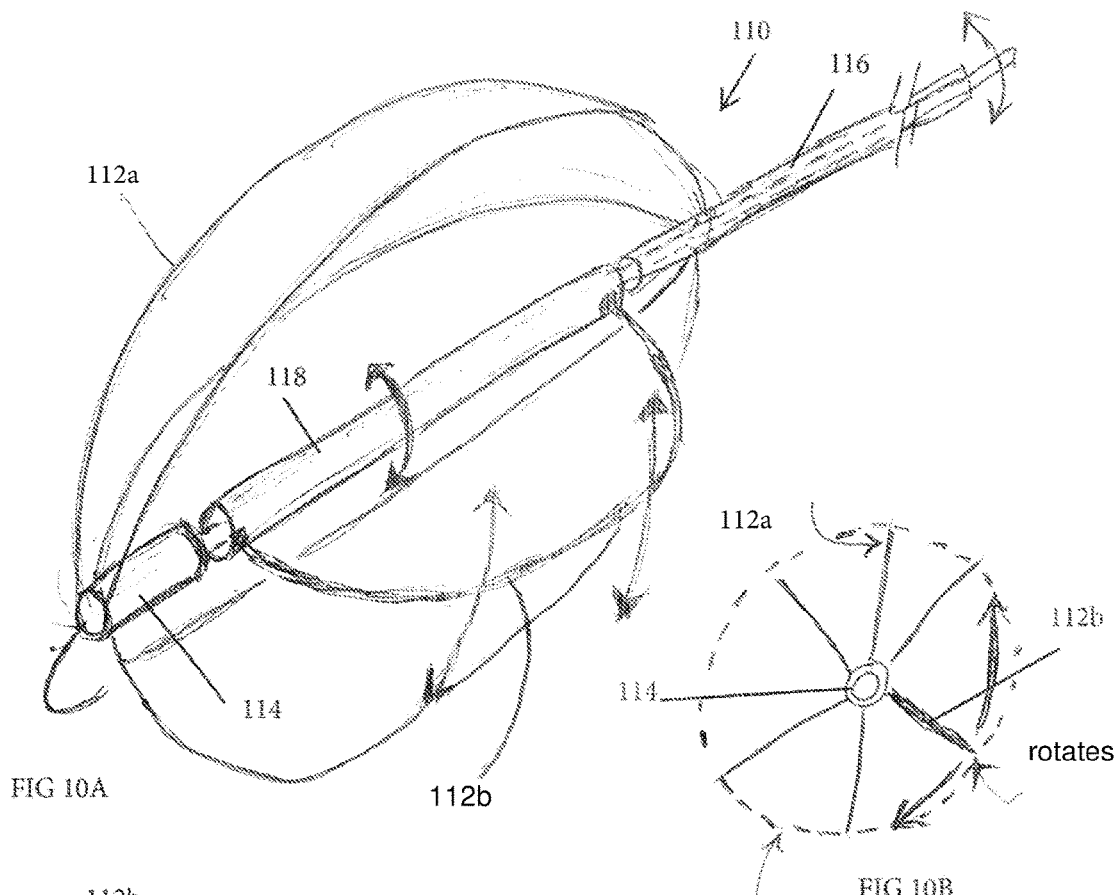
FIG 10A
FIG 10B
vessel wall
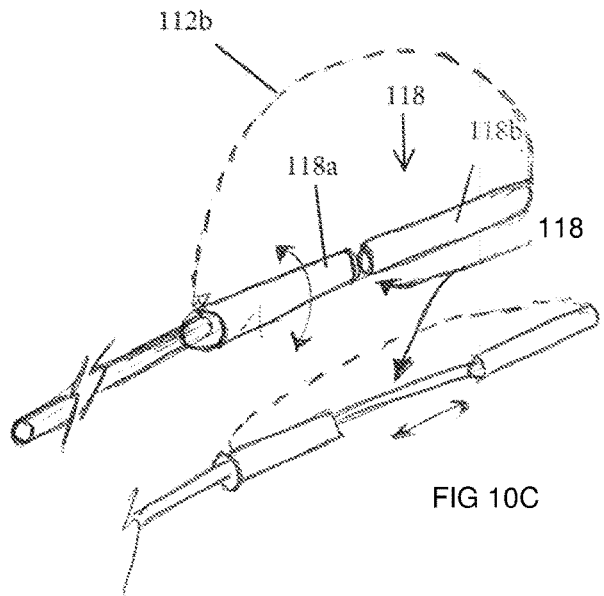
FIG 10C

  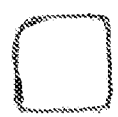
FIG 19A     FIG 19B     FIG 19C
 
FIG 20A     FIG 20B

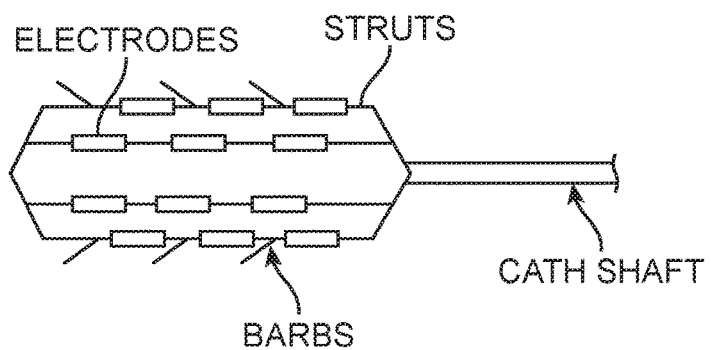
FIG. 21
   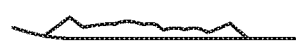
FIG. 22A     FIG. 22B     FIG. 22C     FIG. 22D
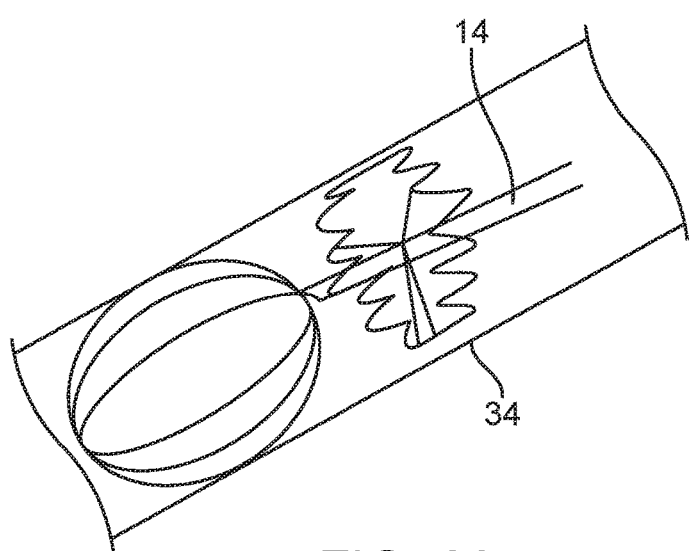
FIG. 23

ELECTRODES AND ELECTRODE POSITIONING SYSTEMS FOR TRANSVASCULAR NEUROMODULATION

This application claims the benefit of the following US Provisional Applications, each of which is incorporated herein by reference: U.S. 62/034,144, filed Aug. 6, 2014, U.S. 62/034,146, filed Aug. 6, 2014, U.S. 62/034,149, filed Aug. 6, 2014, U.S. 62/034,152, filed Aug. 6, 2014, U.S. 62/034,142, filed Aug. 6, 2014, and U.S. 62/036,526, filed Aug. 12, 2014.

TECHNICAL FIELD OF THE INVENTION

The present application generally relates to arrangements of electrodes and associated methods for performing neuromodulation using electrodes disposed within the vasculature.

BACKGROUND

Co-pending U.S. application Ser. No. 13/547,031 entitled System and Method for Acute Neuromodulation, filed Jul. 11, 2012; the "'031 application", filed by an entity engaged in research with the owner of the present application, is attached at the Appendix and incorporated herein by reference. The '031 application describes a system which may be used for hemodynamic control in the acute hospital care setting, by transvascularly directing therapeutic stimulus to parasympathetic nerves and/or sympathetic cardiac nerves using electrodes positioned in the superior vena cava (SVC). In disclosed embodiments, delivery of the parasympathetic and sympathetic therapy decreases the patient's heart rate (through the delivery of therapy to the parasympathetic nerves) and elevates or maintains the blood pressure (through the delivery of therapy to the cardiac sympathetic nerves) of the patient in treatment of heart failure.

Co-pending US application Ser. No. 14/642,699 (the '699), filed Mar. 9, 2015 and U.S. Ser. No. 14/801,560 (the '560), filed Jul. 16, 2015, each incorporated by reference, describe transvascularly directing therapeutic stimulus to parasympathetic and/or sympathetic cardiac nerves using electrodes positioned in the SVC, right brachiocephalic vein, and/or left brachiocephalic vein and/or other sites. As with the system disclosed in the '031, the methods disclosed in these applications can decrease the patient's heart rate (through the delivery of therapy to the parasympathetic nerves) and elevate or maintain the blood pressure (through the delivery of therapy to the cardiac sympathetic nerves) of the patient in treatment of heart failure.

The '699 and '560 applications describe one form of catheter device that may be used to perform transvascular neuromodulation. In particular, these applications shows a support or electrode carrying member 10 of the type shown in FIG. 1A on the distal part of a catheter member 14. The electrode carrying member 10 includes a plurality of struts 12. One or more of the struts carries one or a plurality of electrodes 17. The electrode carrying member 10 is designed to bias such electrodes into contact with the vessel wall. The electrodes 17 may be carried by the struts 12 in a variety of ways. For example, the electrodes may be mounted to or formed onto a substrate 15 that is itself mounted onto a strut or a plurality of struts, or the struts might be flex circuits including the electrodes, or the electrodes might be formed or deposited directly onto the struts. The material forming the struts 12 may have a shape set or shape memory that aids in biasing the circumferentially-outward facing surfaces (and thus the electrodes) against the vessel wall. The struts 12 or substrates 15 might utilize materials or coatings that allow the electrodes' active surfaces (those intended to be placed against the vascular wall) to be exposed, but that insulate the remainder of each electrode's surface(s) against loss of stimulation energy into the blood pool. In some embodiments, the struts 12 or substrate may be formed of an insulative substrate such as a polymer (including silicone, polyurethanes, polyimide, and copolymers) or a plastic. The electrodes can be constructed onto the strut or substrate using a variety of manufacturing techniques, including subtractive manufacturing processes (such as mechanical removal by machining or laser cutting), additive processes (such as laser sintering, deposition processes, conductor overmolding), or combinations (such as printed circuit technology with additive plating). In some embodiments, the struts and electrodes may be flex circuit or printed circuit elements.

As shown in FIG. 1B and as discussed in the '699 and '560, one strut may carry a plurality of electrodes, and those electrodes may be arranged in various configurations having different electrode densities and patterns.

In transvascular neuromodulation, including that described in the '031 application, it is important that the electrodes be properly positioned relative to the target nerve (s) in order to capture the target nerve fibers, while avoiding collateral stimulation of non-target nerve fibers. Mapping procedures are typically performed at the time of electrode placement within the vasculature, and may be repeated during therapy, to identify and/or fine tune the optimal electrode location. Mapping can be manually controlled by the clinician or automatically controlled by the neuromodulation system. During mapping, different electrodes, combinations of electrodes, or arrays can be independently energized while the target response to the stimulus is monitored. For stimulation relating to cardiac or hemodynamic function, parameters such as heart rate, blood pressure, ventricular inotropy and/or cardiac output might be monitored. In some cases mapping includes additional steps of repositioning the electrode carrying member so as to allow additional electrode sites to be sampled. The mapping process is performed until the optimal electrode or combination of electrodes for the desired therapy array is identified.

This application describes various electrode arrangements or arrays that may be used on an electrode support or strut for transvascular neuromodulation. The present application also describes electrode support configurations that allow the longitudinal and/or circumferential electrode position to be adjusted within a blood vessel without requiring repositioning of the entire electrode support.

This application also describes various electrode designs that may be used for transvascular neuromodulation. The electrodes may be used on electrode supports or struts of the type shown in FIGS. 1A-1C, or on catheters or other types of supports. In certain embodiments, electrode designs allow or promote the washing of blood between the conductive electrode surface and the surrounding vascular wall, so as to minimize accumulation or formation of organic material on the electrode surface where it can act as an insulator and thus impair energy delivery. In other designs, the electrodes are shaped to promote even current density. This application also describes electrode supports having retention features engageable with the surrounding vascular wall so as to maintain the electrodes in a stable position for the duration of therapy.

In transvascular neuromodulation, including that described in the '031 application, it is important that the intravascular electrodes be properly positioned sufficiently close to the target nerve(s) outside the vessel so as to capture the target nerve fibers. The present application also describes electrode support configurations that distend the vascular wall so as to bring the intravascular electrodes into proximity with the target nerve structures outside the vessel.

The electrode systems, support configurations, electrodes etc disclosed herein may be used in chronically-implantable or acute neuromodulation systems for carrying out transvascular nerve stimulation.

BRIEF DESCRIPTION OF THE DRAWINGS

FIGS. 3A through 3C schematically illustrate three examples of the orientations a pair of nerves positioned external to a blood vessel might lie in.

FIG. 10A is a perspective view of a distal portion of a catheter system having a electrode-carrying strut that is rotatable to adjust the circumferential position of the electrodes on the strut.

FIG. 10B is an end view of the electrode carrying member of FIG. 10A illustrating rotation of the rotatable strut.

FIG. 10C is a perspective view illustrating an alternative configuration to the support member shown in FIG. 10A.

FIGS. 19A through 19C are top views of electrodes shaped for even current density.

FIGS. 20A and 20B are cross-section views of electrodes shaped for even current density.

FIG. 21 illustrates an intravascular electrode carrying member including retention features that engage the surrounding walls of a blood vessel.

FIGS. 22A-22D are side elevation views of various types of retention features that may be used on an electrode carrying member.

FIG. 23 shows an alternative retention feature for use with an electrode carrying member.

DESCRIPTION

The present application shows and describes various features for use on electrode systems of the type used to transvascularly stimulate nerves located outside the vasculature by energizing one or more electrode pairs of the electrode system.

FIGS. 2A through 9B of the present application show and describes various arrangements in which electrodes may be positioned on a common strut or on a common substrate carried by a strut. The term "array" as used herein will mean a plurality of electrodes carried on a common strut or substrate. Thus, on an electrode support 10 of the type shown in FIGS. 1A and 1B, a plurality of electrodes disposed on strut 12a will be considered an array, and a plurality of electrodes disposed on strut 12b will be considered a separate array. A plurality of electrodes on a common substrate is likewise an array, even if that substrate spans more than one strut as shown in FIG. 1C.

Figure 2A:
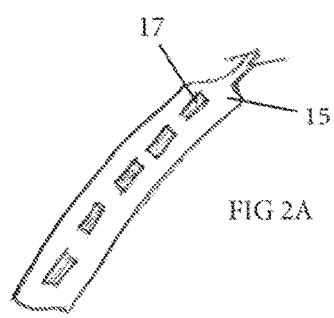
FIGS. 2A and 2B illustrate two examples of arrangements of electrodes into arrays.

FIG. 2A illustrates one exemplary array, in which a plurality of electrodes are positioned to have a longitudinal orientation—such that direction of the electric field created when electrode pairs are activated extends generally parallel to the direction of blood flow through the vessel and the longitudinal axis of the vessel. If the electrodes are ones having a long axis and a short axis as with the illustrated rectangular electrodes, the long axis may be oriented such that it is parallel to the longitudinal axis of the vessel as shown, or it may extend perpendicular to the longitudinal axis of the vessel (see the orientation of the FIG. 2B electrodes). While the array includes one elongate column of electrodes, the array might instead include two or more columns of electrodes.

Figure 2B:
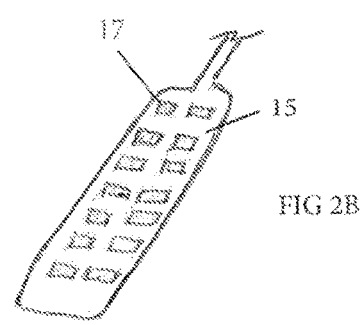

FIG. 2B illustrates an array in which a plurality of electrodes are arranged in multiple columns and multiple rows, allowing a longitudinally oriented field as described for FIG. 2A (if electrodes in a common column are activated) while providing the alternative that two electrodes in the same row may be energized to create a resulting electric field extending orthogonally to the direction of blood flow and the longitudinal axis of the vessel. The energized electrode pair might also be electrodes that are oriented diagonally from one (e.g. in the FIG. 2B embodiment, the first electrode in the first column and the second electrode in the second column), resulting in an electric field oriented at an angle that is neither 180 degrees nor 90 degrees with respect to the direction of blood flow.

This arrangement also increases electrode surface area relative to the FIG. 2A embodiment, gives close edge-to-edge positioning of the electrodes, and thus allows capture of small-diameter/fine nerves while minimizing collateral stimulation. This figure shows two columns of electrodes, although alternatives range from a single column to three or more columns. Additionally, although rectangular electrodes are shown, the electrodes of the FIGS. 2A and 2B embodiments may have a variety of other shapes, including (without limitation) elliptical, circular, square, polygonal etc.

Different current densities and patterns may be beneficial based on the type and location of nerves, and the orientation of the nerve relative to the array.

Figure 9A:
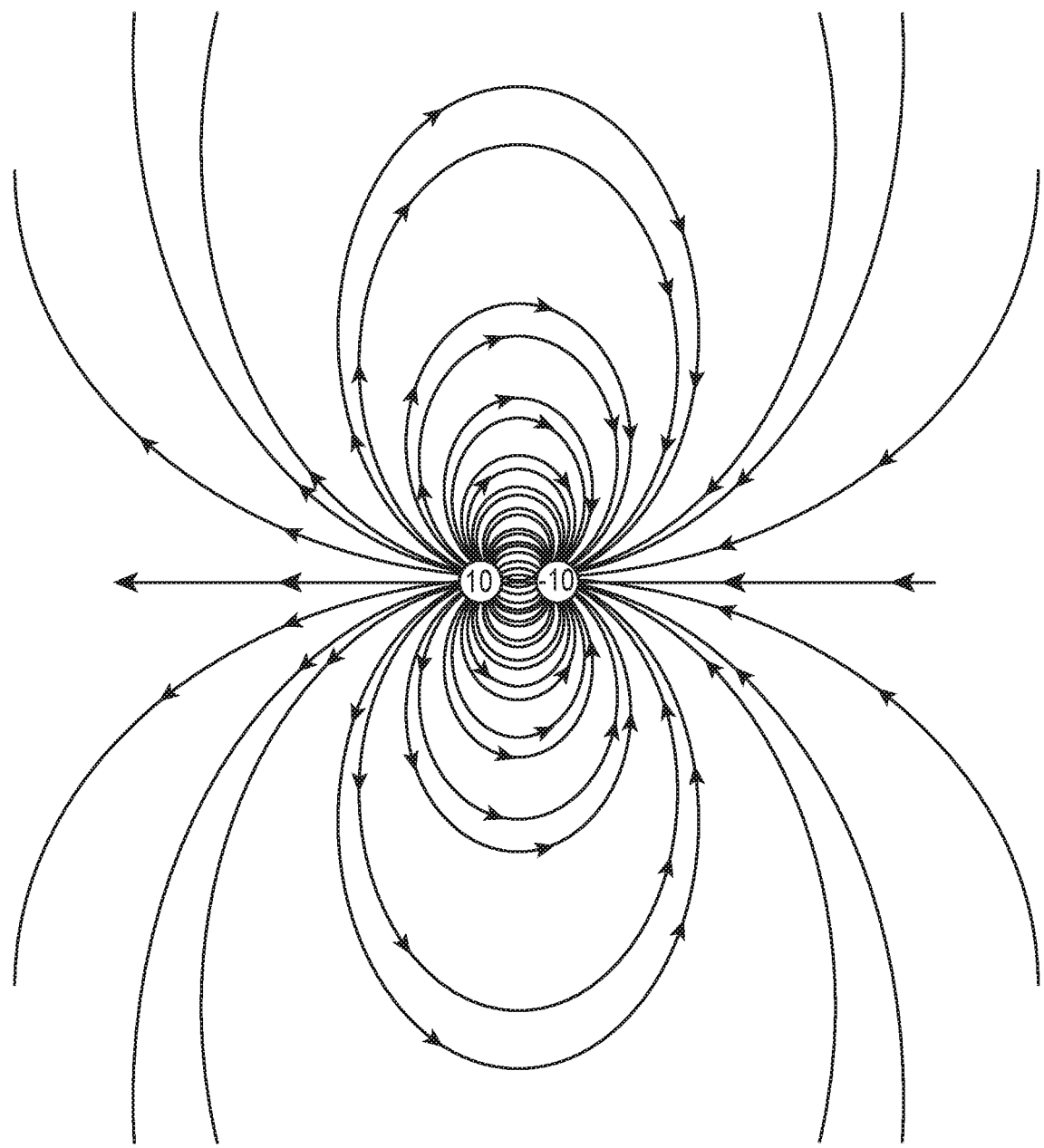
FIG. 9A illustrates an electric field generated by a closely spaced electrode pair.
Figure 9B:
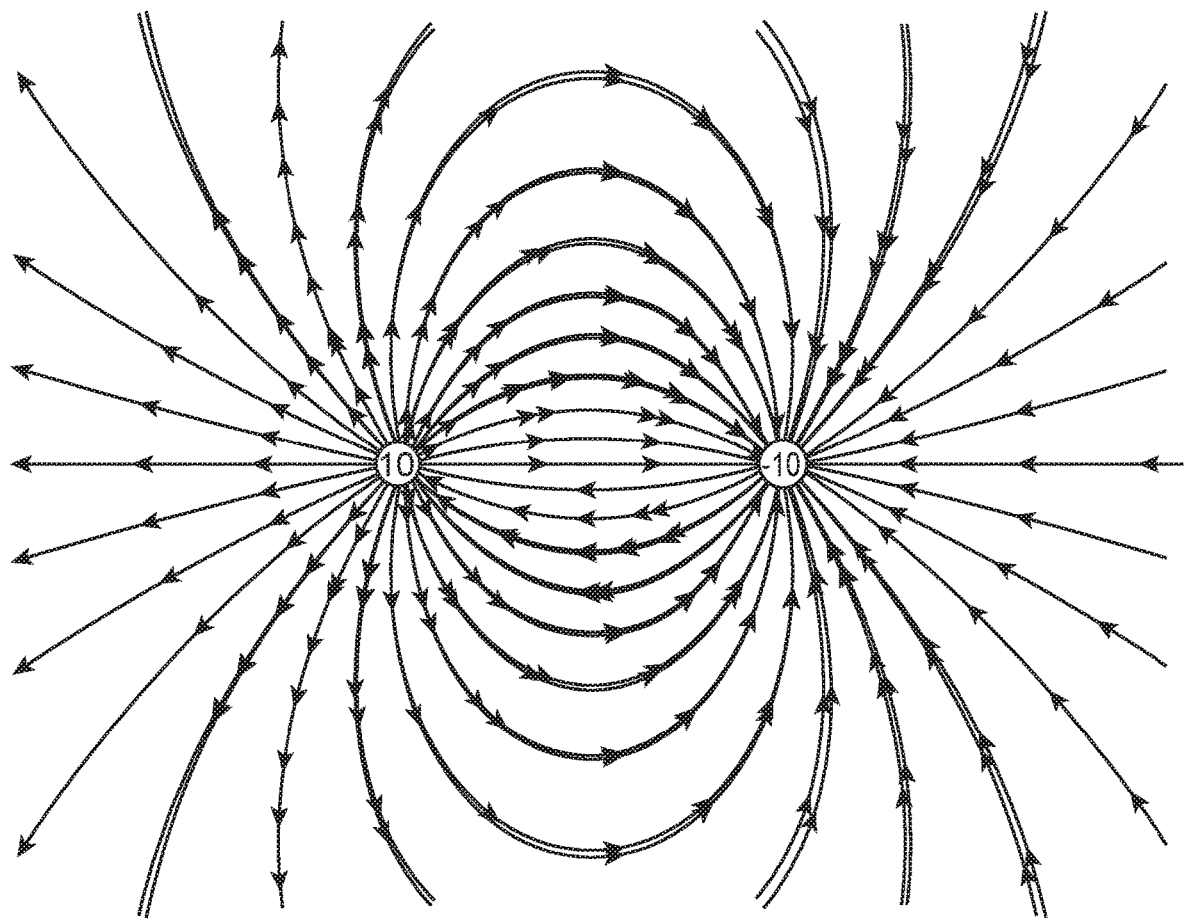
FIG. 9B illustrates an electric field generated by an electrode pair spaced by a much greater distance than that of FIG. 9A.

Stimulating using tightly spaced electrodes (e.g. 1 mm edge-to-edge separation between electrodes in both the longitudinal and lateral direction, as applicable) can be beneficial for reducing collateral stimulation and increasing the specificity of nerve selection. Tightly spaced electrodes emit a more narrow and concentrated electric field (See FIG. 9A) compared with the broader and less dense electric field produced by electrodes that are far apart (FIG. 9B). This improves the ability of the neuromodulation system to select (through mapping) and focus energy on a target nerve that may be positioned in close proximity to other nerve fibers. It also avoids the "broadcasting effect" occurring when electrodes are spaced far apart and thus minimizes chance that collateral (non-target) nerves or muscles will be captured.

As discussed in the '031 and '699 applications, neuromodulation for treatment of heart failure can involve capture of both parasympathetic nerves and cardiac sympathetic nerves from within a common blood vessel, such as the SVC or the left brachiocephalic vein. In accordance with one method of capturing such nerve, a single array of the type shown in FIGS. 2A and 2B may be employed to capture both target nerves.

Figure 3A:
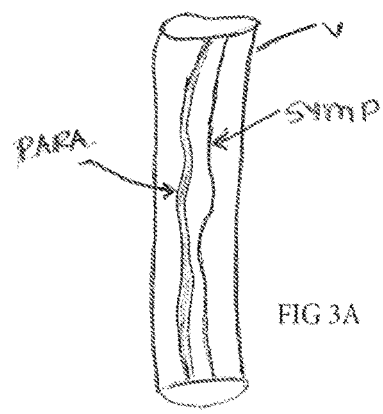
Figure 3B:
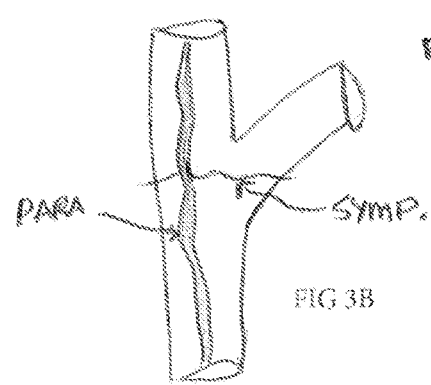
Figure 3C:
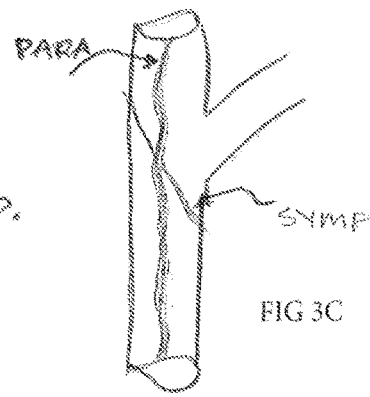

FIGS. 3A-3C illustrate possible orientations of a target parasympathetic nerve PARA and a target cardiac sympathetic nerve SYMP outside of a vessel V within which the array could be positioned. As shown, nerve PARA might run generally parallel to the direction of blood flow and longitudinal axis of the vessel, while the nerve SYMP might itself be parallel (FIG. 3A), perpendicular (FIG. 3B), or otherwise angled (FIG. 3C) relative to the direction of blood flow and longitudinal axis of the vessel.

FIGS. 4A through 6B schematically illustrate electrode arrays of the type shown in FIGS. 2A and 2B disposed within a blood vessel. The FIGS. 4A and 4B blood vessels have adjacent nerves in the orientations shown in FIG. 3A, the FIG. 5A/5B blood vessels have adjacent nerves in the orientations shown in FIG. 3B, and the FIG. 6A/6B blood vessels have adjacent nerves in the orientations shown in FIG. 3C. These drawings illustrate the various relative orientations of the nerves and active electrode pairs that can be used to stimulate them.

Figure 4A:
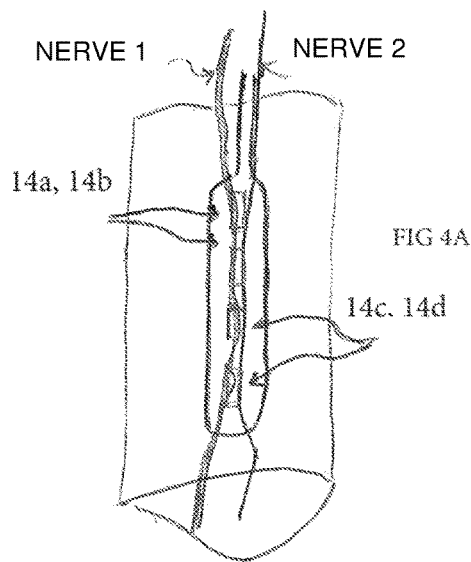
FIGS. 4A and 4B show exemplary methods of capturing nerves arranged as in FIG. 3A using the electrode arrangements of FIGS. 2A and 2B, respectively.
Figure 4B:
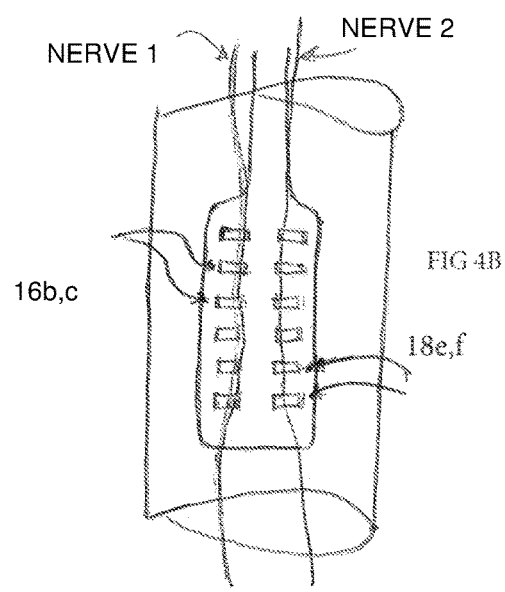

To capture nerves arranged as in FIG. 3A using an electrode configuration of the type shown in FIG. 2A, a first pair 14*a, b* is activated to capture one of the parallel nerves and a second pair of electrodes 14*c, d* is activated to capture the other parallel nerve (FIG. 4A). To capture the nerves of the FIG. 3A arrangement using the FIG. 2B array, a first pair of electrodes 16*b, c* within one of the columns of electrodes in the array may be activated to capture one of the parallel nerves, and a second pair of electrodes 18*e, f*in the same or a different column are activated to capture the other parallel nerve (FIG. 4B).

Figure 5A:
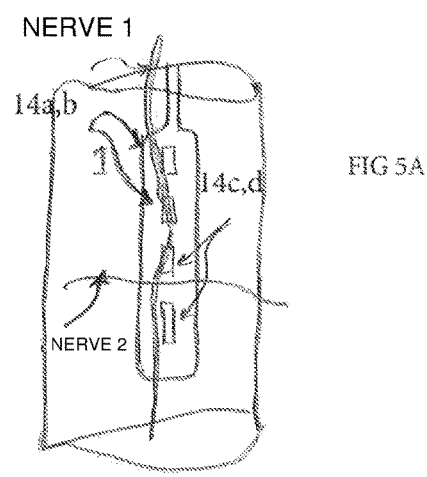
FIGS. 5A and 5B show exemplary methods of capturing nerves arranged as in FIG. 3B using the electrode arrangements of FIGS. 2A and 2B, respectively.
Figure 5B:
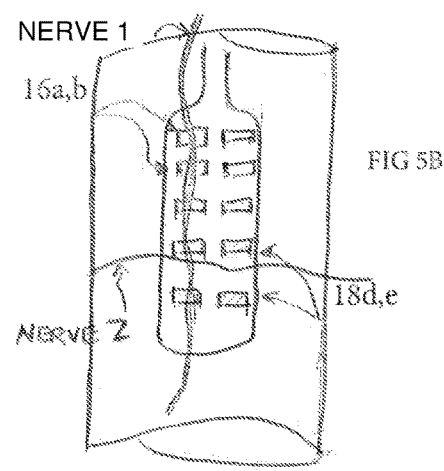

To capture nerves arranged as in FIG. 3B using an electrode configuration of the type shown in FIG. 2A, a first pair 14*a,b* along the nerve is activated to capture the parallel nerve and a second pair of electrodes 14*c,d* (each on an opposite side of the nerve) is activated to capture the perpendicular nerve (FIG. 5A). To capture the nerves of the FIG. 3B arrangement using the FIG. 2B array, a first pair of electrodes 16*a, b* within one of the columns of electrodes in the array may be activated to capture the parallel nerve, and a second pair of electrodes 18*d, e* in the same or a different column are activated to capture the perpendicular nerve (FIG. 5B).

Figure 6A:
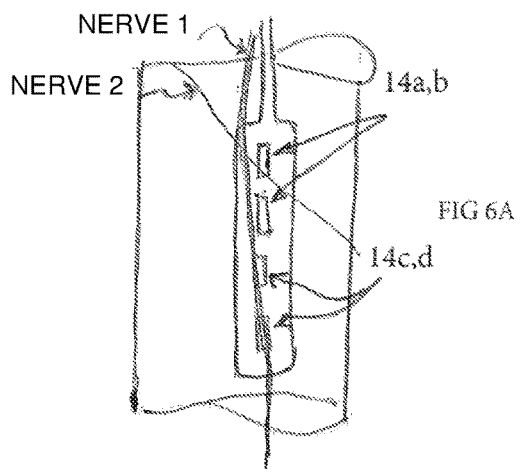
FIGS. 6A and 6B show exemplary methods of capturing nerves arranged as in FIG. 3C using the electrode arrangements of FIGS. 2A and 2B, respectively.
Figure 6B:
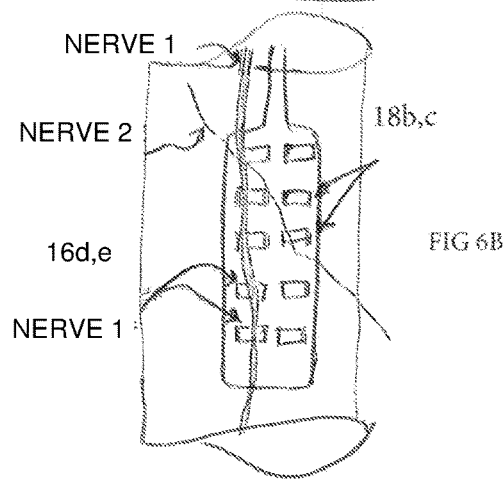

To capture nerves arranged as in FIG. 3C using an electrode configuration of the type shown in FIG. 2A, a first pair 14*c, d* is activated to capture the parallel nerve and a second pair of electrodes 14*a, b* is activated to capture the angled nerve (FIG. 6A). To capture the nerves of the FIG. 3C arrangement using the FIG. 2B array, a first pair of electrodes 16*d, e* within one of the columns of electrodes in the array may be activated to capture the parallel nerve, and a second pair of electrodes 18*b, c* in the same or a different column are activated to capture the perpendicular nerve (FIG. 6B).

Figures 7A, 7B, 7C:
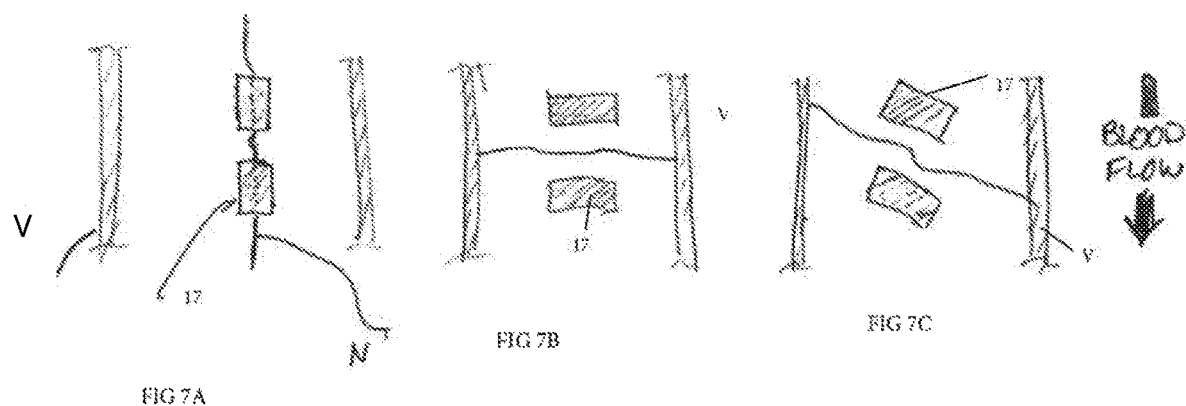
FIGS. 7A through 7C illustrate three examples of the orientation of nerves relative to the direction of blood flow in a blood vessel, together with corresponding electrode pair orientations that might be suitable for stimulating the illustrated nerves.
Figures 8A, 8B, 8C:
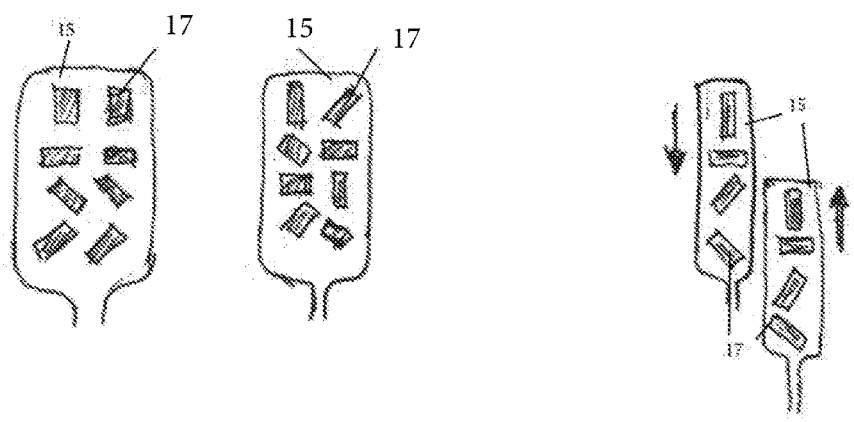
FIGS. 8A through 8C illustrate electrode arrays having electrodes positioned in a variety of orientations.

For electrode arrays employing rectangular electrodes (or other electrode shapes such as elliptical shapes that have a long axis and a short axis), the electrodes pairs in an array that will most optimally capture a given nerve target may depend on the orientation of the nerve target. For example, optimal capture might occur using electrode pairs in which each electrode's long axis is generally parallel to the orientation of the nerve fiber. Thus, for example, the configuration of FIG. 7A, in which the electrode's 17 long axis runs parallel to the vessel's V longitudinal axis might be useful for capturing a nerve fiber N that runs longitudinally relative to the blood vessel. An orthogonal orientation of the electrode's 17 long axis (i.e. perpendicular to the vessel's longitudinal axis) might be useful for capturing a nerve N running orthogonally to the vessel's longitudinal axis as in FIG. 7B, and a non-orthogonal angular orientation of the electrode's 17 long axis (e.g. one extending diagonally) relative to the vessel's longitudinal axis might be useful for capturing a nerve N running at a non-orthogonal angular orientation as shown in FIG. 7C.

As discussed, mapping procedures are typically conducted during therapy to identify the best electrode pairs for capturing the target nerve. The electrode orientations depicted in FIGS. 7A through 7C may be combined in a single array so that the array will have electrodes in the most beneficial orientation for capture regardless of whether the target nerve has a longitudinal, orthogonal, or angled orientation. The electrodes on such an array may be arranged with like-oriented electrodes sharing a row as in FIG. 8A, or with the electrodes orientations more randomly oriented as in FIG. 8B, or some other arrangement. As a third alternative, a pair of electrode arrays may be positioned in proximity to one another, with one of the arrays being repositionable (e.g. longitudinally slidable relative to the electrode support and other array) so as to create a larger set of possible electrode pairs that can be activated to capture the target nerves.

Adjustable Electrode Positioning

FIGS. 10A-13 application and the accompanying text show and describe intravascular catheter systems used to support and position neuromodulation electrodes within a blood vessel.

The illustrated catheter systems include electrode carrying members carried at the distal end of a catheter member. The catheter member and electrode carrying member are ideally disposed within a deployment sheath that is percutaneously introduced. The distal end of the system is advanced through the vasculature to the blood vessel from within which therapy is to be delivered. The electrode carrying member is then deployed from the deployment sheath into the target blood vessel. The electrode carrying member biases electrodes in contact with the surrounding vascular wall—such that when energy from a neuromodulation system energizes the electrodes, target nerve fibers outside the blood vessel are captured. The disclosed embodiments are designed to position the electrodes in positions suitable for delivering electrical therapy to the target fibers from the intended position of the array within the vasculature. Moreover, once the electrode carrying member is positioned at a desired position within the blood vessel, these embodiments allow the user to circumferentially or longitudinally reposition the electrodes within the vessel in order to optimize the electrode position (such as during mapping or therapy) without relocating the entire electrode carrying member within the blood vessel.

Circumferential Electrode Repositioning

Referring to FIG. 10A, electrode carrying member 110 may be similar to that described above with respect to the '699 application, in its use of a plurality of struts to anchor the electrode carrying member within the vessel and to bias the electrodes into contact with the vessel wall. Struts 112a have a fixed rotational position relative to the longitudinal axis of the electrode carrying member 110, while at least one of the struts 112b is configured to be rotatable relative to the longitudinal axis of the electrode carrying member 110. The rotatable strut 112b carries one or more electrodes, and one or more of the non-rotating struts 112a may also carry electrodes. When the electrode carrying member 110 is deployed in a vessel so that the struts 112a are expanded to anchor against the vessel's walls, rotating the strut 112b relative to the strut 112a adjusts the circumferential position of the corresponding electrodes along the vessel wall.

In the embodiment shown in FIG. 10A, the distal ends of the non-rotatable struts 112a are anchored at the distal hub 114 of the electrode carrying member 110 and the proximal ends are anchored to a tubular catheter body 116. Rotatable strut 112b has first and second ends supported by a support member 118. The distal end of support member 118 is coupled to the distal hub 114 in a manner that permits axial rotation of the support member 118 relative to the distal hub. The proximal end of the support member 118 is connected to a shaft 120 that extends through the tubular catheter body 116 to a proximally positioned handle (not shown). When the user rotates the handle, the shaft 120 and support member 118 axially rotate, thus changing the rotational position of the strut 112b.

In a slightly modified embodiment shown in FIG. 10C, the support member 118 includes a distal segment 118a to which the distal end of the strut 112b is connected and a proximal segment 118b to which the proximal end of the strut 112b is connected. The proximal and distal segments are coupled together such that they simultaneously rotate upon rotation of the handle, but such that at least one may be moved towards/away from the other to lengthen and radially collapse the strut 112b. This allows the strut 112b to be compressed it can be contained within an introducer sheath for insertion into and navigation through a blood vessel.

During use, the electrode carrying member 110 is compressed within an introducer sheath, including by separating the segments 118a, 118b to collapse and lengthen the strut 112b. The introducer sheath with the catheter inside is advanced to a target site within the target blood vessel. The struts 112a, 112b of the electrode carrying member expand within the blood vessel as the introducer sheath is withdrawn from the electrode carrying member. The longitudinal separation between the segments 118a, 118b is decreased to expand the strut 112b into contact with the vessel wall. By rotating the handle, the user can rotate the strut 112b to adjust the circumferential position of the electrodes on the vessel wall while leaving the remaining struts 112a at their original position within the blood vessel.

Longitudinal Electrode Repositioning

Figures 11A, 11B:
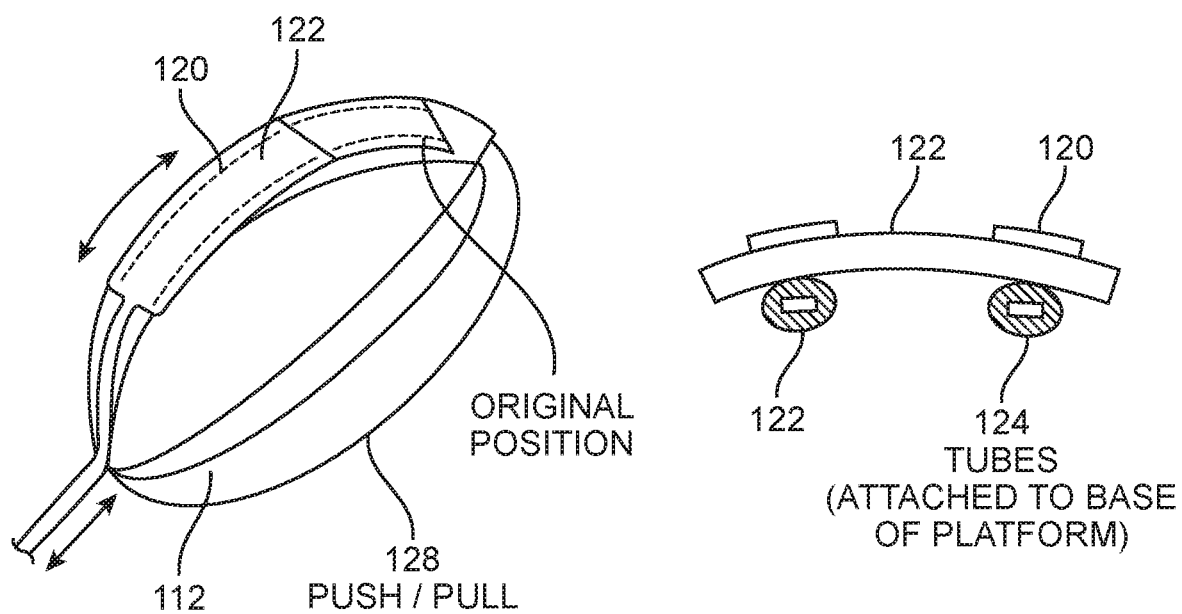
FIG. 11A is a perspective view of a distal portion of a catheter system having a longitudinally slidable electrode array.
FIG. 11B is a cross-section view through the substrate and struts of the system of FIG. 11A.
Figure 11C:
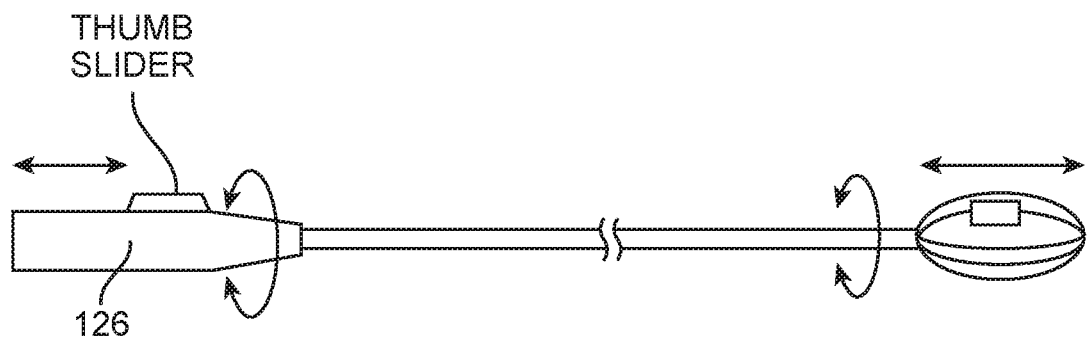
FIG. 11C is a side elevation view of the catheter system of FIG. 11A.

FIG. 11A shows an embodiment of a neuromodulation catheter system in which the longitudinal position of an electrode or electrode array relative to a strut may be adjusted while the electrode carrying member is anchored within a vessel. In this embodiment, the electrodes 120 are positioned or formed on a member 122 which may be a substrate or flex circuit as described above. The member 122 is mounted to one or more tubes 124, each of which is slidably positioned on a strut 112 such that the struts serve as rails for movement of the tubes 124 (and thus member 122 supported on the tube(s) 124). The struts 112 and lumen of the tube(s) 124 preferably have non-circular cross-section so as to prevent to the tubes from rotating on the struts 112.

The catheter includes a proximal handle 126. A push/pull element 128 extends proximally from the member 122 through the catheter body to a slider or other mechanism on the handle for manipulation by a user. Manipulation of the mechanism moves the push/pull element 128 in proximal/distal directions to pull/push the member 122, thus moving the electrodes 120 proximally/distally along the corresponding strut(s) 112. If rotational (circumferential) repositioning of the electrodes within the blood vessel is desired, the user may apply torque to the handle so as to cause corresponding rotation of the catheter body and electrode carrying member 10.

Figure 12A:
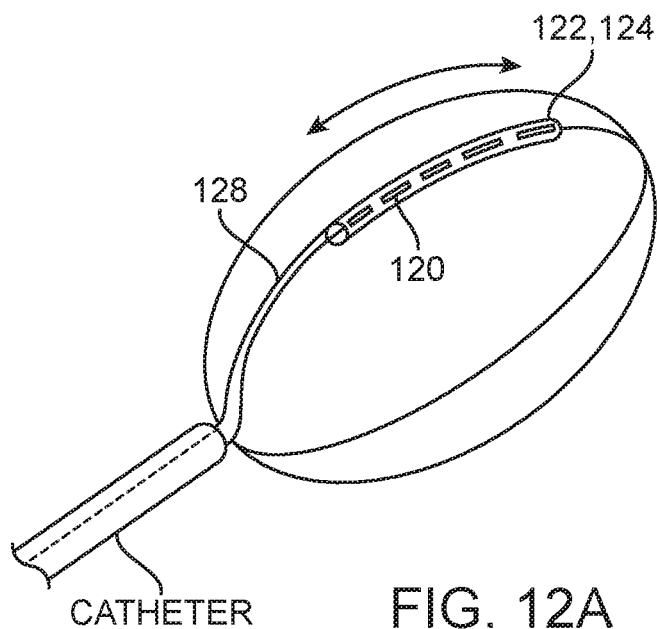
FIG. 12A is a perspective view of a distal portion of a second embodiment of a catheter system having a longitudinally slidable electrode array.
Figure 12B:
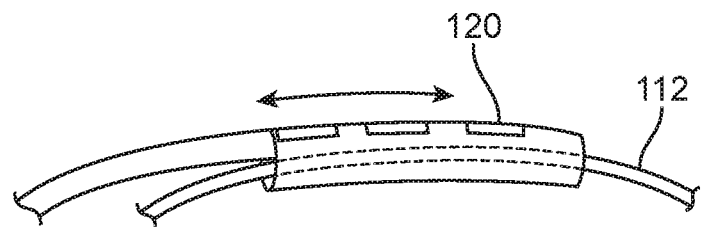
FIG. 12B is a detailed view of the strut and tube assembly of FIG. 12A.

In an alternative embodiment shown in FIGS. 12A and 12B, the member 122 and tube 124 take the form of a tube 122,124 having electrodes 120 positioned thereon. A push/pull element 128 may take the form or a wire or mandrel connected to the tube 124, or it may be a proximal portion of the tube 128 which has been longitudinally cut to form a curved strip as shown in FIG. 12B.

Figure 13:
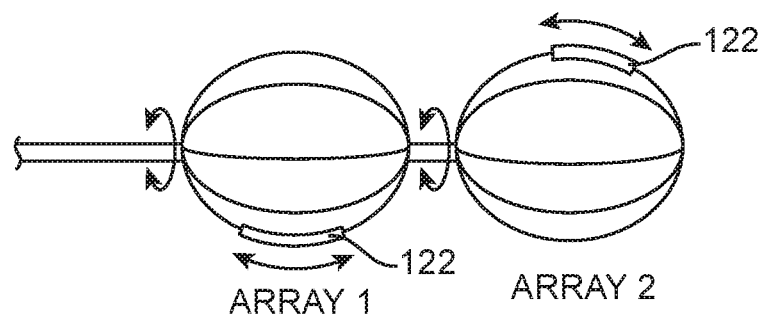
FIG. 13 illustrates a catheter system having telescoping arrangement of electrode carrying members having longitudinally slidable arrays.

FIG. 13 illustrates that two catheters of the second embodiment may be placed in a telescoping arrangement, thus placing two or more longitudinally and rotationally repositionable arrays within a vessel or pair of vessels.

Electrode Designs

FIGS. 14A through 20B and the accompanying text show and describe various electrode designs that may be used on an electrode support, strut, catheter or other support used for transvascular neuromodulation. In certain embodiments, electrode designs allow or promote the washing of blood between the electrode surface facing the vessel wall and the adjacent vessel wall, so as to minimize accumulation or formation of organic material on the electrode surface where it can act as an insulator and thus impair energy delivery. In other designs, the electrodes are shaped to promote even current density. This application also describes electrode supports having retention features engageable with the surrounding vascular wall so as to maintain the electrodes in a stable position for the duration of therapy.

Blood Washing of Electrodes

Figure 1A:
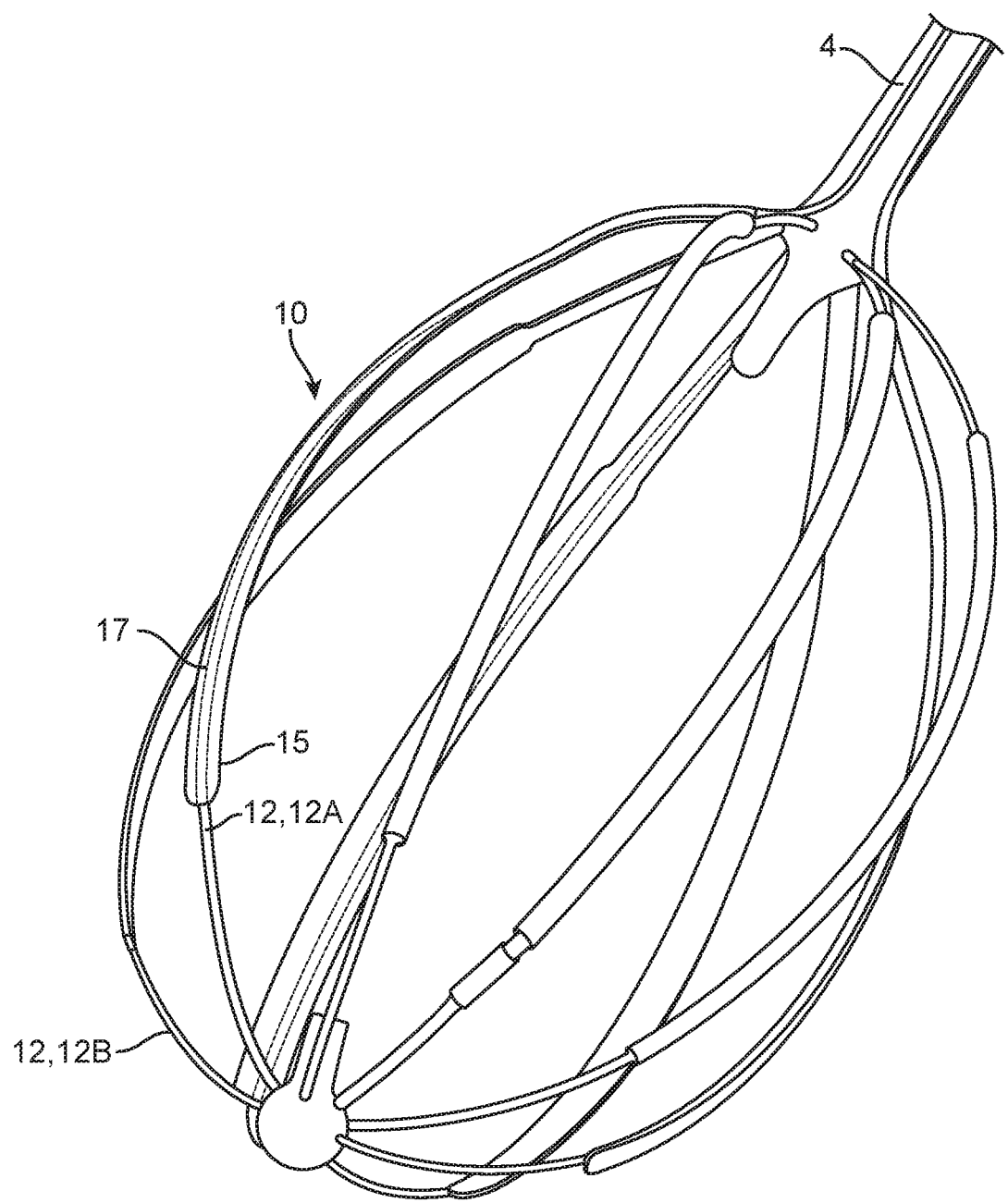
FIGS. 1A through 1C show electrode carrying members of the type shown in the '699 and '560 applications, with electrodes carried thereon.
Figure 1B:
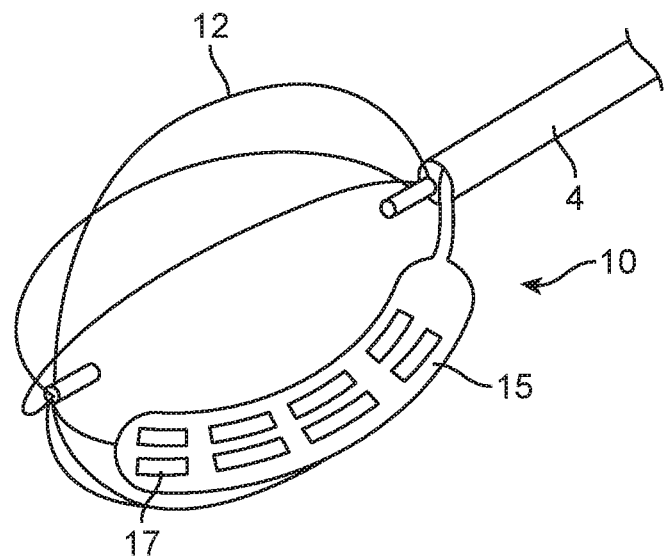
Figure 1C:
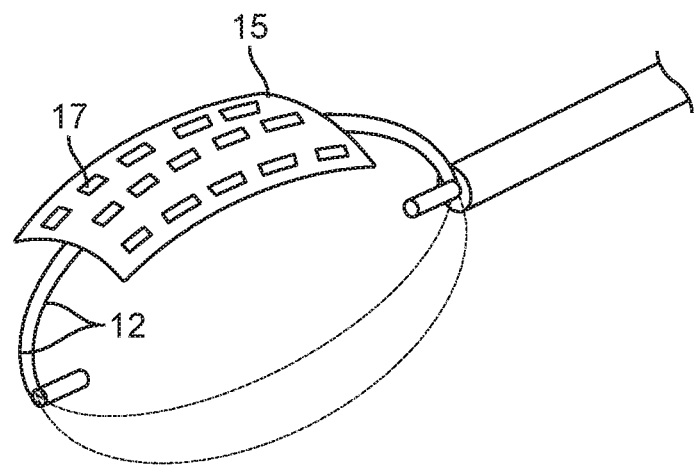

Electrode embodiments shown in FIGS. 14A through 18 may be positionable on electrode carrying members 10 of the type describe with reference to FIGS. 1A through 1C, such as by mounting the electrodes on the struts 12. However, these embodiments may be used on other types of catheters or electrode carrying members designed to support electrodes with the active electrode surface facing a vascular wall for the purpose of delivering therapy to target nerve structures outside the vascular wall.

Figure 14A:
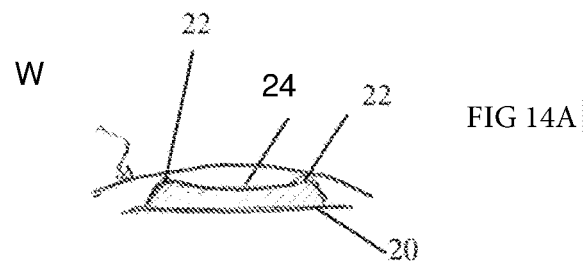
FIG. 14A is a cross-section view of a first electrode design shaped for blood washing over the electrode surface.
Figure 14B:
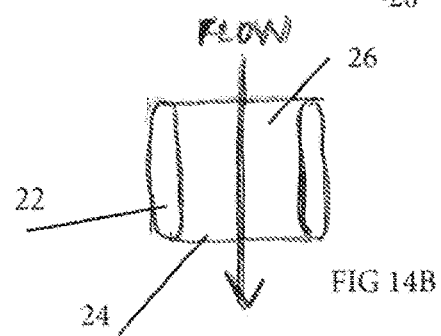
FIG. 14B is a top view of the electrode of FIG. 14A.
Figure 15:
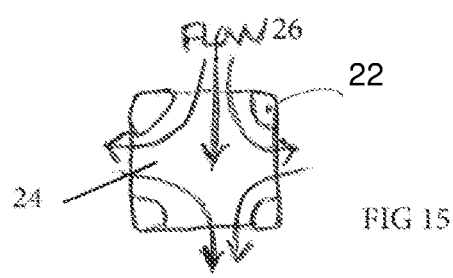
FIG. 15 is a top view of a second electrode design.
Figure 16:
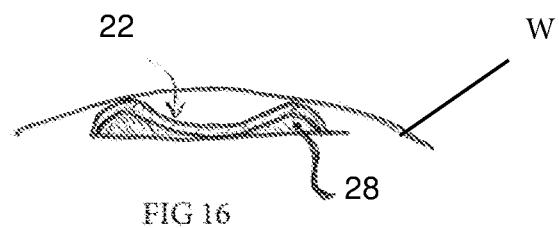
FIG. 16 is a cross-section view of a third electrode design.
Figure 17A:
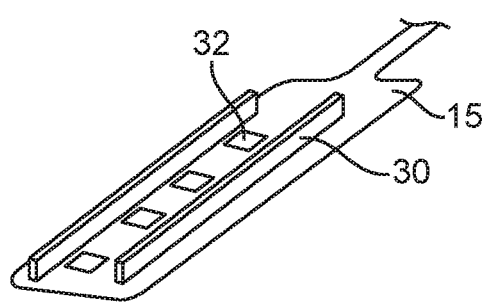
FIG. 17A is a perspective view of a substrate having electrodes and stand-off features.
Figure 17B:
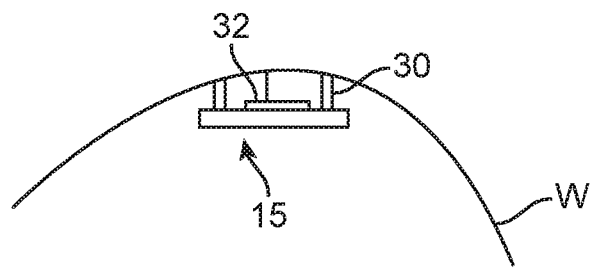
FIG. 17B is a cross-section view of the substrate of FIG. 17B.
Figure 18:
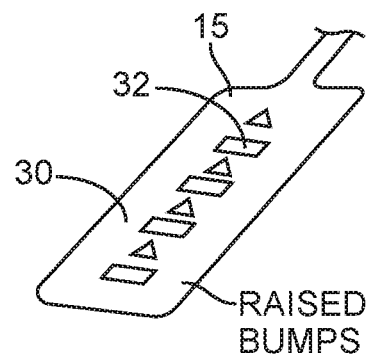
FIG. 18 is a perspective view of a second embodiment of a substrate having electrodes and stand-off features.

In the embodiments of FIGS. 14A through 16, the illustrated electrodes 20 each include a first portion 22 positionable in contact with the interior surface of the wall W of the vessel within which the electrode is positioned. A second portion 24 of the electrode is recessed from the first portion 22 such that when the first portion 22 is in contact with the wall W, the second portion 24 defines one or more flow pathways 26 between the second portion 24 and the wall W. In the FIGS. 14A and 14B embodiment, the first portion 22 defines raised edge regions that, when the electrode is in contact with the wall W, extend generally parallel to the direction of blood flow within the vessel. In the FIG. 15 embodiment, the first portion 22 defines raised corner portions of a square or rectangular electrode, allowing blood to enter/exit the space between the second portion and the wall W along multiple flow pathways 26. The FIG. 16 embodiment, the electrode surface is formed on or mounted to a concave insulative backing. In each of the exemplary embodiments, the electrode material itself may be formed to have the desired shape as shown in FIGS. 14A-15, or an insulative substrate or backing 28 on the electrode may provide the shape to the first and second portions 22, 24 as in FIG. 16. Smooth transitions between the first and second portions 22, 24 may be included so as to prevent accumulation of thrombotic material in sharp corner regions.

In alternative embodiments, flow pathways between electrodes and the vessel wall may be created using stand-off features 30 on the supports that carry the electrodes, such as on substrates 15 of the type shown in FIG. 1B, or on splines 12 (FIG. 1A), or on catheters upon which the electrodes are carried. In the FIG. 17A/17B embodiment, the stand-off features 30 comprise one, two or more elongate rails mounted on substrate 15 and positionable in contact with the vessel wall W. The rails define a flow-pathway that is parallel to the direction of blood flow. The electrodes 32 are shown positioned between the rails but might alternatively or additionally be positioned on the opposite sides of the rails. In the FIG. 18 embodiment, the stand-off features 30 comprise a plurality of raised elements, some of which may be disposed between adjacent electrodes. In other embodiments (not shown), electrodes are disposed in channels on the substrate surface, so that when the substrate 15 is positioned in contact with the vessel wall, the electrodes remain off-set from the vessel walls and flow pathways are defined between the vessel wall and the interiors of the channels, again allowing flowing blood to wash over the electrode surfaces.

Promotion of Even Current Density

FIGS. 19A-19C are plan views showing electrode shapes that may be used to deliver therapy in a transvascular neuromodulation system. In general, the shapes are ones that are generally free from sharp corners. Thus the circular (FIG. 19A), elliptical (FIG. 19B), or square, rectangular or other polyhedral shapes having rounded corners (FIG. 19C) may be used.

Promotion of even current density may also be enhanced by forming the electrodes to have cross-sections that are also free of corners, such as the dome shape of FIG. 20A or the shape of FIG. 20B which has a generally planar or gently curved tissue contact surface and beveled edges transitioning to the electrode carrying member, support (e.g. strut) or substrate.

Engagement/Retention Features

During transvascular stimulation, the intravascular electrode carrying member may be susceptible to movement as a result of cardiac movement, respiratory movement or blood flow. Because minor movements of an electrode positioned to capture a nerve can result in loss of that nerve capture, it is desirable to minimize the susceptibility of the electrodes to movement. Electrode carrying members, struts etc. that carry electrodes for transvascular stimulation may thus be equipped with engagement features that can engage the interior of the vascular wall when the electrode carrying member is deployed at a target stimulation site.

As shown in FIG. 21, an electrode carrying member 10 may be provided with engagement elements such as hooks (FIG. 22A), barbs (FIG. 22B), small barbs, wires or filaments (FIG. 22C), or roughened surface regions (FIG. 22D). The electrode carrying member 10 might include a variety of different elements, or similar elements made from different materials, to increase the chances that some of the elements will engage the electrode carrying member to the vascular wall. A sheath positioned over the electrode carrying member 10 may be used to prevent contact between the engagement elements and the vascular wall during insertion of the electrode carrying member and, for certain types of engagement elements such as barbs, can keep the elements in a compressed state and allow them to spring into engagement with the vessel wall when the sheath is withdrawn.

In addition, or as an alternative to, the engagement features, the catheter member 4 supporting the electrode carrying member may include an expandable anchor 34 (FIG. 23) that is expandable into contact with the vascular wall, thus providing an additional anchoring structure (supplemental to anchoring provided by the struts of the electrode carrying member).

Electrode Positioning Systems and Methods

FIGS. 24-27 and the accompanying text describe intravascular electrode carrying members used to support and position neuromodulation electrodes within a blood vessel, and to distend a portion of the blood vessel so as to bring the electrodes into closer proximity with the target nerve.

The FIGS. 24-27 catheter systems include electrode carrying members carried at the distal end of a catheter member. The catheter member and electrode carrying member are ideally disposed within a deployment sheath that is percutaneously introduced. The distal end of the system is advanced through the vasculature to the blood vessel from within which therapy is to be delivered. The electrode carrying member is then deployed from the deployment sheath into the target blood vessel. The electrode carrying member biases electrodes in contact with the surrounding vascular wall—such that when energy from a neuromodulation system energizes the electrodes, target nerve fibers outside the blood vessel are captured.

Figure 24:
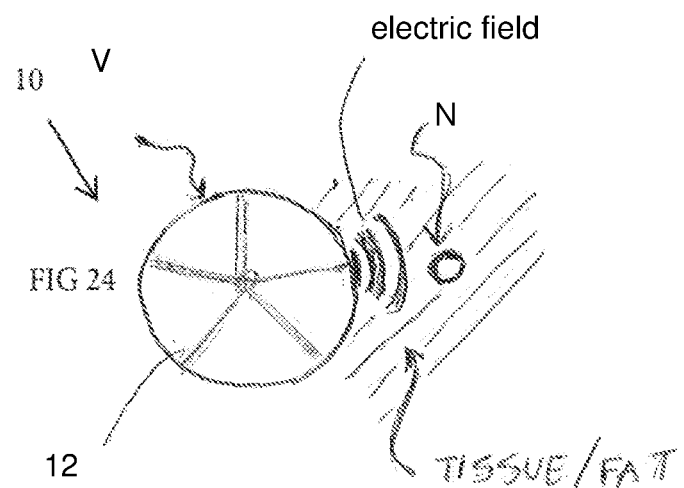
FIG. 24 schematically shows a cross-section of a blood vessel with a catheter system positioned for neuromodulation of a target nerve outside the vessel, as well as tissue and fat surrounding the vessel.

FIG. 24 is a transverse cross-section view of a blood vessel, showing an electrode carrying member 10 having radial struts 12. As illustrated, in this example the target nerve N is spaced sufficiently far from the exterior wall of the blood vessel V that energy from the electric field created by electrodes on the array cannot reach the nerve.

Figure 25:
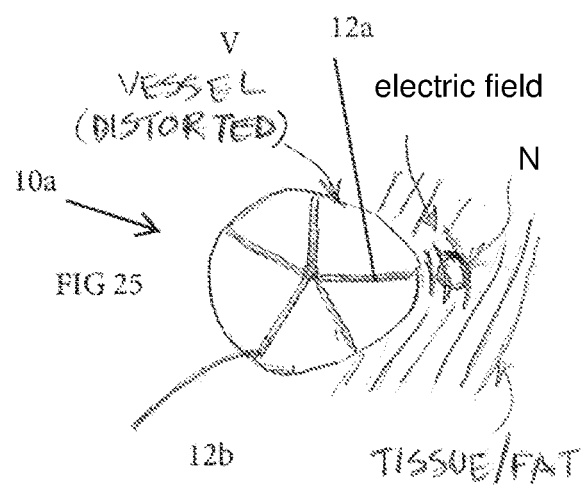
FIG. 25 is similar to FIG. 24 but shows a catheter system distending the vessel wall towards the target nerve.
Figure 26:
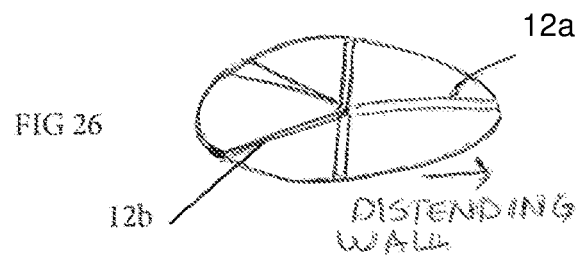
FIG. 26 is an end view showing an electrode carrying member of a catheter system of the type shown in FIG. 25.

Referring to FIG. 25, a modified electrode carrying member 10a includes features that distend the portion of the vessel wall V at which the electrodes are located towards the target nerve N to thereby decrease the distance between the electrodes and the target nerve. This therefore decreases the distance the electric field must travel in order to stimulate the nerve. The electrodes are preferably on strut that distends the vessel wall in order to minimize the distance between the active electrodes and the target nerve.

The electrode carrying member may have an asymmetrical configuration, with the strut 12a supporting the electrodes extending further in a radial direction than the remaining struts 12b. Alternatively or additionally, the strut 12a may possess greater strength in the radial direction than that struts 12b, so that when the electrode carrying member is placed in a vessel of smaller diameter than the electrode carrying member, the vessel will prevent the struts 12b from radially expanding beyond the vessel diameter, but the strut 12a will have sufficient strength for pressing the adjacent vessel wall outwardly. The struts 12b opposite to the strut 12a will be constructed to provide a reactionary force to that of the strut 12a. See FIG. 26.

Figure 27:
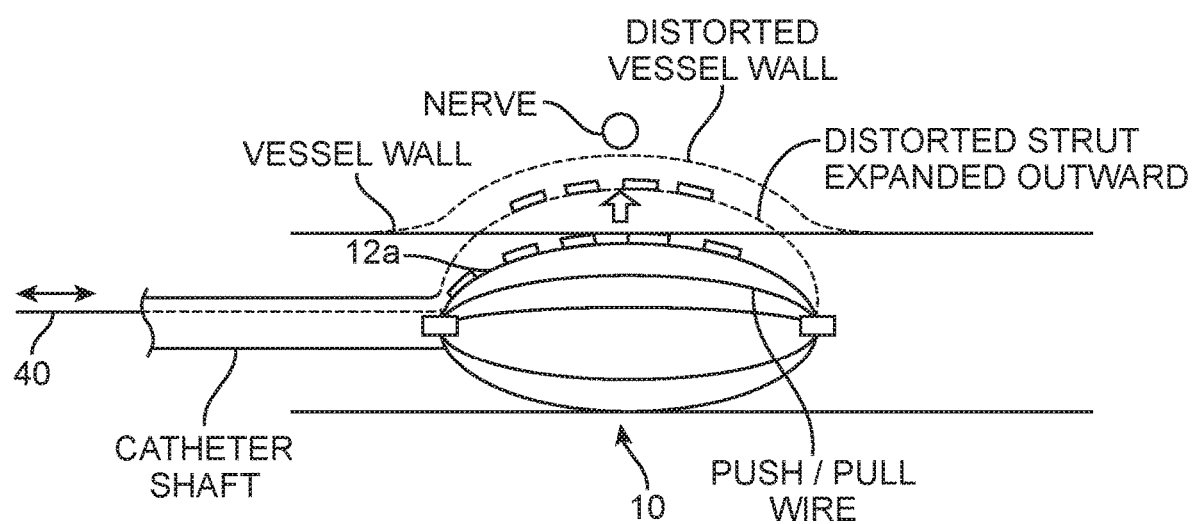
FIG. 27 illustrates a second embodiment of a catheter system capable of distending the vessel wall towards the target nerve.

In an alternative embodiment shown in FIG. 27, the electrode carrying member 10 includes struts that may be actively moved radially outwardly so as to distend the vessel wall. For example, an electrode carrying strut 12a may have a controlling wire/rod 40 connected to it. The wire/rod 40 extends to the proximal end of the catheter (e.g. at a handle having a control slider, knob etc). The user can push the wire/rod distally to cause the strut 12a to extend in the direction of the vessel wall, thus tenting the vessel wall and moving the electrodes carried by the strut 12a closer to the target nerve as depicted in FIG. 27.

Additional Embodiments

It should be understood and appreciated that the various features described herein may be combined in a variety of ways. For example, any of the various electrodes, electrode arrangements, stand-off features, retention features, distension features, etc. described in the application, may be used in various combinations on any of the electrode supports described elsewhere in the application. Such combinations of features are considered to be embodiments encompassed within the scope of the present disclosure.

All patents and patent applications referred to herein, including for purposes of priority, are incorporated herein by references for all purposes.

We claim:

1. An electrode system for transvascular stimulation of nerve targets, comprising:
    an electrode support including a plurality of longitudinally extending struts, said electrode support expandable within a blood vessel to position said struts in contact with an interior wall of the blood vessel;
    electrodes carried on at least one of the struts;
    wherein the electrode support has a deployed position within a blood vessel wherein at least one of the struts extends further from a longitudinal axis of the electrode support, in a radial direction, than the other struts in the plurality of struts so as to asymmetrically deform the blood vessel wall so that the portion of the blood vessel wall contacting said at least one strut distends towards the nerve target, wherein said at least one strut possesses greater strength in a radial direction relative to a longitudinal axis of the electrode support than the other struts in the plurality of struts.

2. An electrode system for transvascular stimulation of nerve targets, comprising:
    an electrode support including a plurality of longitudinally extending struts, said electrode support expandable within a blood vessel to position said struts in contact with an interior wall of the blood vessel;
    electrodes carried on at least one of the struts;
    wherein the electrode support has a deployed position within a blood vessel wherein at least one of the struts extends further from a longitudinal axis of the electrode support, in a radial direction, than the other struts in the plurality of struts so as to asymmetrically deform the blood vessel wall so that the portion of the blood vessel wall contacting said at least one strut distends towards the nerve target, wherein said at least one strut is actively moveable in a radially outward direction independently of the other struts so as to distend said portion of the blood vessel towards the nerve target.

3. The electrode system of claim 2, wherein said at least one strut includes a control wire or rod having a first end extending to the proximal end of the catheter, said control wire or rod manually moveable to move said at least one strut in the radially outward direction.

* * * * *